United States Patent [19]

Oliu et al.

[11] Patent Number: 5,322,047
[45] Date of Patent: Jun. 21, 1994

[54] TEMPERATURE COMPENSATED AIR/FUEL RATIO CONTROLLER AND METHOD THEREFOR

[75] Inventors: Joaquin Oliu, Boca Raton; Donald A. Weaver, Lauderhill; Dudley D. Nye, Fort Lauderdale, all of Fla.

[73] Assignee: Dynalco Controls, Inc., Ft. Lauderdale, Fla.

[21] Appl. No.: 119,348

[22] Filed: Sep. 9, 1993

[51] Int. Cl.[5] ............................................. F02D 41/14
[52] U.S. Cl. .................................... 123/676; 123/694
[58] Field of Search ........................ 123/676, 693, 694

[56] References Cited

U.S. PATENT DOCUMENTS

| | | | |
|---|---|---|---|
| 3,915,135 | 10/1975 | Kushida et al. | 123/694 |
| 4,030,462 | 6/1977 | Sasayama et al. | 123/694 |
| 4,150,562 | 4/1979 | Nielsen | 123/694 X |
| 4,156,404 | 5/1979 | Anzai | 123/694 |
| 5,033,438 | 7/1991 | Feldinger et al. | 123/694 |

FOREIGN PATENT DOCUMENTS 3937 1/1991 Japan ................................ 123/676

OTHER PUBLICATIONS

AF-1000 Series Air/Fuel Ratio Controllers for Carbureted Engines, Published 1992, by Dynalco Controls of Ft. Lauderdale, Fla.
AF-1011 Air/Fuel Ratio Controller for Single Bank, Carbureted, Naturally Aspirated Engines, Product Manual, Published Aug., 1991, by Dynalco Controls of Ft. Lauderdale, Fla.

Primary Examiner—Tony M. Argenbright
Attorney, Agent, or Firm—Cesarano & Kain

[57] ABSTRACT

The temperature compensated air/fuel ratio controller is used in conjunction with an internal combustion engine. The method includes electronically sensing the oxygen content and the temperature of the exhaust gas generated by the engine. It was discovered that the oxygen content signal varies in a curvilinear manner with respect to the temperature. The oxygen content signal is therefore compensated in both the linear and non-linear signal regions. The compensated oxygen content signal is then used to control the air/fuel ratio of the engine. In a working embodiment, the temperature compensated air/fuel ratio controller utilizes a zirconium oxide oxygen sensor. One type of circuitry designed to compensate the oxygen content signal in both the linear and non-linear signal regions includes, in one embodiment, electronic circuitry that segments the curvilinear function into linear segments and generates a plurality of linear compensatory signals which are added to the oxygen content signal. The compensated oxygen signal is then applied to a PID controller in the control loop of the engine.

20 Claims, 4 Drawing Sheets ns from the engine are reduced to a minimal level. Also,
TEMPERATURE COMPENSATED AIR/FUEL RATIO CONTROLLER AND METHOD THEREFOR The present invention relates to an air/fuel ratio controller, used in conjunction with internal combustion engines, which is supplied with a temperature compensated oxygen exhaust gas signal.

BACKGROUND OF THE INVENTION

Air/fuel ratio controllers are used to regulate the flow (particularly the pressure) of fuel fed to internal combustion engines. Some of these air/fuel ratio controllers are incorporated in a feedback control loop for the engine in order to maintain a constant percentage of oxygen in the engine's exhaust. By maintaining oxygen exhaust gas at a constant level, undesirable emissions from the engine are reduced to a minimal level. Also, catalytic converters in the engine's exhaust system are designed to operate at certain oxygen content levels. By maintaining a certain oxygen content, the converter operates in its optimal range. The air/fuel ratio controller is used in conjunction with an oxygen sensor and a temperature sensor, which are both exposed to the exhaust gas emitted by the internal combustion engine. After filtering the electronic signals generated by these sensors, prior art air/fuel ratio controllers compensated the oxygen signal in a linear manner by monitoring the temperature. In other words, the prior art devices were designed to operate under the assumption that above a certain cut-off temperature, the oxygen sensor varied linearly with temperature. In one prior art device, after the linear compensation of the oxygen content signal, that signal was fed into a proportional, integral, derivative control circuit whose output was coupled to a valve driver. The control signal output by the valve driver was fed directly to the fuel pressure regulator for the internal combustion engine.

OBJECTS OF THE INVENTION

It is an object of the present invention to provide temperature compensation for the oxygen content sensor used in conjunction with a air/fuel ratio controller.

It is another object of the present invention to provide temperature compensation for the non-linear variation of the oxygen content signal.

It is a further object of the present invention to compensate the oxygen content signal using low power electrical components.

It is an additional object of the present invention to provide temperature compensation for the oxygen content signal with the use of discrete electrical components.

It is another object of the present invention to provide linear and non-linear temperature compensation for the oxygen content signal which may be used in conjunction with microprocessor based air/fuel ratio control systems.

SUMMARY OF THE INVENTION

The temperature compensated air/fuel ratio controller is used in conjunction with an internal combustion engine. The method includes electronically sensing the oxygen content and the temperature of the exhaust gas generated by the engine. It was discovered that the oxygen content signal varies in a curvilinear manner with respect to the temperature. The oxygen content signal is therefore compensated in both the linear and non-linear signal regions. The compensated oxygen content signal is then used to control the air/fuel ratio of the engine. In a working embodiment, the temperature compensated air/fuel ratio controller utilizes a zirconium oxide oxygen sensor. One type of circuitry designed to compensate the oxygen content signal in both the linear and non-linear signal regions includes, in one embodiment, electronic circuitry that segments the curvilinear function into linear segments and generates a plurality of linear compensatory signals which are added to the oxygen content signal. The compensated oxygen signal is then applied to a PID controller in the control loop of the engine.

BRIEF DESCRIPTION OF DRAWINGS

Further objects and advantages of the present invention can be found in the detailed description of the preferred embodiments when taken in conjunction with the accompanying drawings in which.

DETAILED DESCRIPTION OF THE PREFERRED EMBODIMENTS

The present invention relates to an air/fuel ratio controller which is used in conjunction with carbureted internal combustion engine. In order to operate the engine such that the oxygen content of the exhaust gas is maintained at a substantially constant level, prior art devices have used zirconium oxide sensors. However, prior art control feedback loops were designed based upon the theory that the electrical signal representing the oxygen content of the exhaust gases varied linearly dependent upon the temperature of the exhaust gases. For example, in FIG. 1, the oxygen content signal $O_2$ in millivolts is generally linear at exhaust gas temperatures above 800° F. Prior art control feedback loops were based upon the theory that the oxygen content signal varied linearly with respect to the temperature of the exhaust gases at all temperatures above the 600° F. lower cut-off temperature.

It was discovered that, at temperatures generally below 775° F., the signal from a zirconium oxide oxygen sensor varies in a non-linear manner with respect to the exhaust gas temperature. This discovery that oxygen content signal varies both linearly and non-linearly with respect to the temperature (above the 600° F. cut-off) is graphically illustrated in FIG. 1. Prior to this discovery of the non-linear relationship between $O_2$/-

Temp, designers compensated the oxygen content signal in a linear fashion as shown by single line compensatory signal segment 12. Alternatively, designers could raise the cut-off temperature, shown by line 14, from approximately 600° F. to approximately 800° F.

Figure 1:
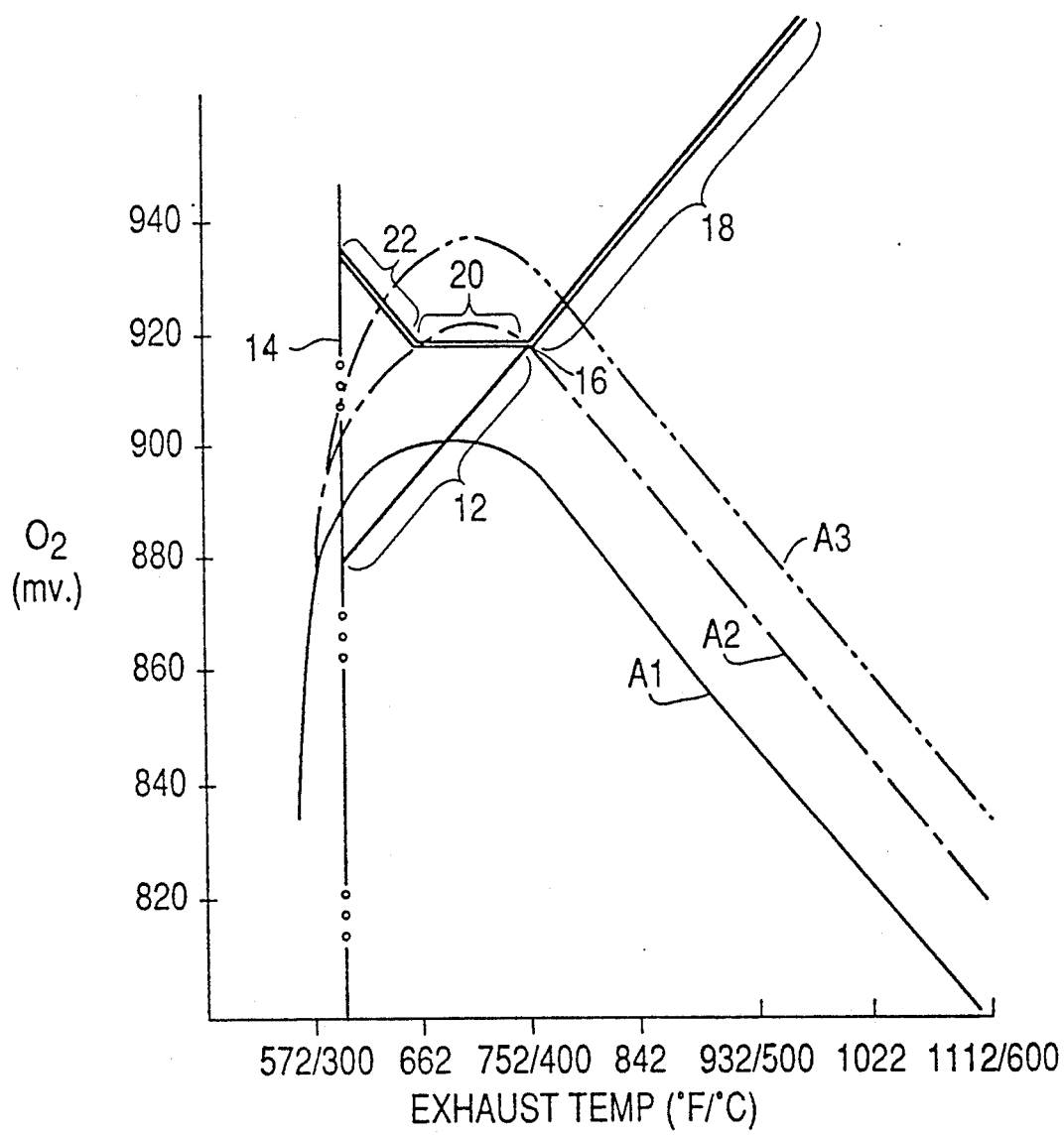
FIG. 1 illustrates the newly discovered curvilinear relationship between the oxygen content signal and the exhaust temperature signal.

Above approximately 800° F., that is, beyond intersection point 16 in FIG. 1, the oxygen content signal is linearly compensated as shown by the linear segment 18 of the double line compensatory signal.

In order to further perfect air/fuel ratio controllers, experiments were conducted with zirconium oxide oxygen sensors manufactured by Autolite of Fostoria, Ohio. These tests showed that the electrical output of these oxygen sensors varied non-linearly in a region approximately below 800° F. and above the cut-off temperature of 600° F. In FIG. 1, solid line A1, single dashed line A2, and double dashed line A3 represent lambda values equal to 0.99, 0.98, and 0.97, respectively. Lambda is generally representative of the oxygen content in exhaust gases, as is known in the art.

Once the non-linear behavior of the zirconium oxide oxygen sensors below 800° F. was discovered, an electronic circuit could be constructed to provide non-linear compensation to this oxygen content signal. In general, the non-linear compensation circuit, in one embodiment, segments the curvilinear function of the $O_2$/Temp into linear segments to generate linear compensatory signal segments 18, 20 and 22. Since curves A1, A2, and A3, representing constant oxygen content levels in the exhaust gas, generally follow the same curvilinear function (other than a constant level shift), the compensatory signal developed by the circuit follows, in one working embodiment, double line signal segments 22, 20 and 18. When this compensatory signal is added to the $O_2$ sensor output, the result is a voltage which remains constant for changing exhaust temperatures.

Figure 2:
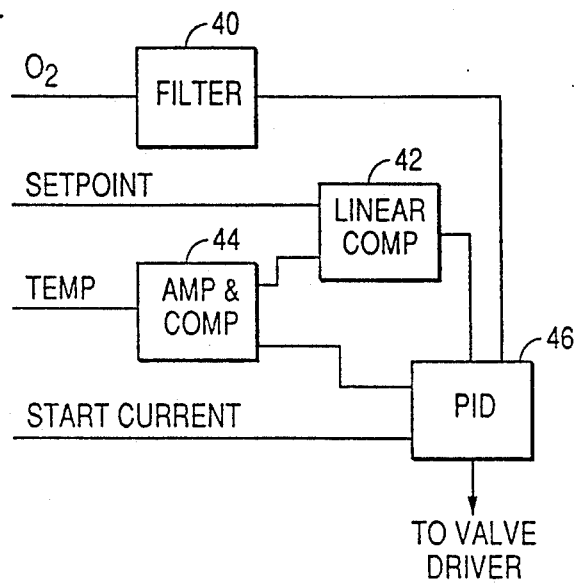
FIG. 2 diagrammatically illustrates a prior art compensation circuit.

FIG. 2 illustrates a block diagram of the prior art linear compensation circuit. The oxygen content signal $O_2$ was fed to filter 40 which generally smooths out the signal. Preferably, filter 40 is an active filter. The temperature signal was fed to an amplifier-comparator unit 44. The comparator established a lower temperature cut-off value, for example, that value illustrated by line 14 in FIG. 1. Amplification was necessary in order to condition the signal for further processing. The output of amplifier circuit 44 is applied to linear compensation circuit 42. Circuit 42 modifies the set point to correspond to the change in $O_2$ sensor output caused by changing exhaust temperatures. The output of circuit 40 and the compensated set point from circuit 42 are applied to proportional integral derivative PID circuit 46. The output of PID 46 was fed to a valve driver. Below approximately 600° F., the comparator output of circuit 44 disables PID circuit 46 and the operator input start current is sent to the valve driver.

Figure 3:
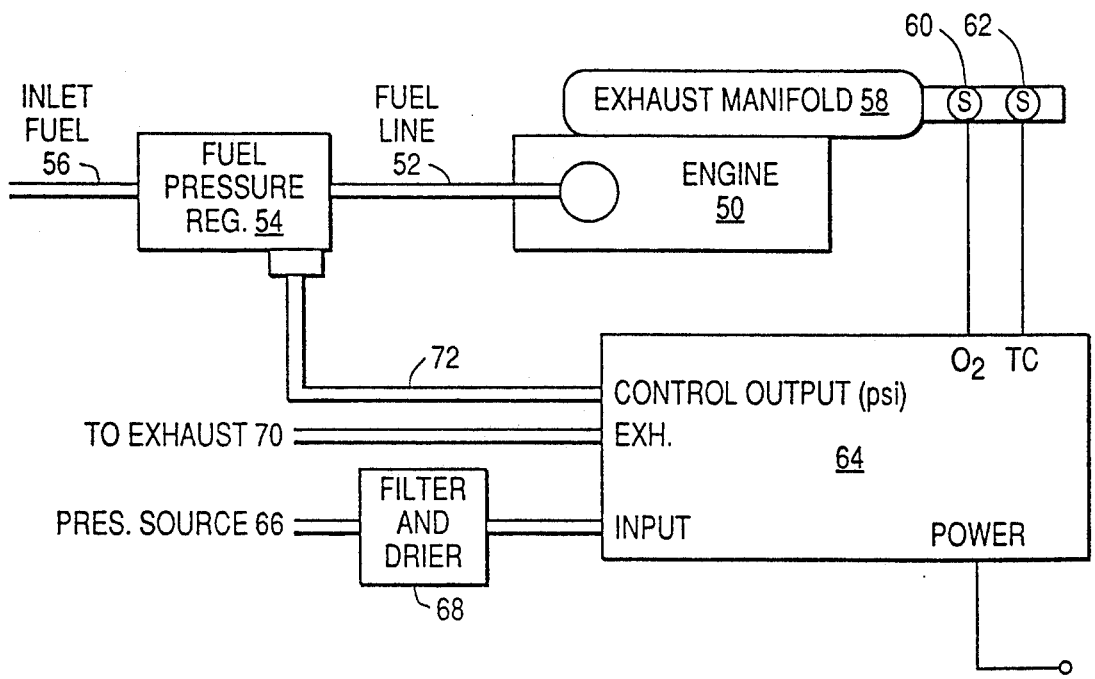
FIG. 3 diagrammatically illustrates an air/fuel ratio controller as part of a feedback control loop for an internal combustion engine.

FIG. 3 diagrammatically illustrates the feedback control loop for internal combustion engine 50. Engine 50 is supplied with fuel via fuel line 52. The pressure and/or flow of fuel is regulated by fuel pressure regulator 54. Fuel is fed to regulator 54 via inlet fuel line 56. Exhaust gases are emitted from engine 50 into exhaust manifold 58. In a working embodiment, a zirconium oxide oxygen sensor 60 and a temperature sensor or thermocouple 62 are exposed to exhaust gases exiting exhaust manifold 58. As such, the oxygen content and the temperature of the exhaust gases are represented as electrical inputs into controller 64. Controller 64 also obtains power from, in one working embodiment, a magnetic pickup. This power is generally in the range of 50–80 milliwatts at approximately 3–4 volts AC RMS. In one working embodiment, a Dynalco magnetic pickup model M208 is used to generate power from internal combustion engines having a flywheel with six pitch or coarser gear teeth. The pickups may be mounted on a bracket or in a tapped hole in the housing near the flywheel.

Controller 64 is also fed with a pressurized gas, either air or natural gas, from a pressure source 66. A filter and a dryer 68 conditions this pressure input. Excess gas is exhausted from controller 64 at pressure exhaust port to exhaust 70. The control output signal on line 72 is a pressure signal which is supplied via conduit 72 directly to the control input port on the fuel pressure regulator 54.

The air/fuel ratio controller diagrammatically illustrated in FIG. 3 and the associated feedback control loop is the same as the prior art/fuel ratio controller. One prior art air/fuel ratio controller is discussed in detail in the Dynalco Controls brochure for Models AF-1011, 1012, 1021, and 1022. Dynalco Controls manufactures these prior art air/fuel ratio controllers in Ft. Lauderdale, Fla.

The present invention incorporates a non-linear oxygen compensation circuit into controller 64 in order to compensate the oxygen content electrical signal and generate compensatory signal segments 22, 20 and 18 shown in FIG. 1.

Figure 4:
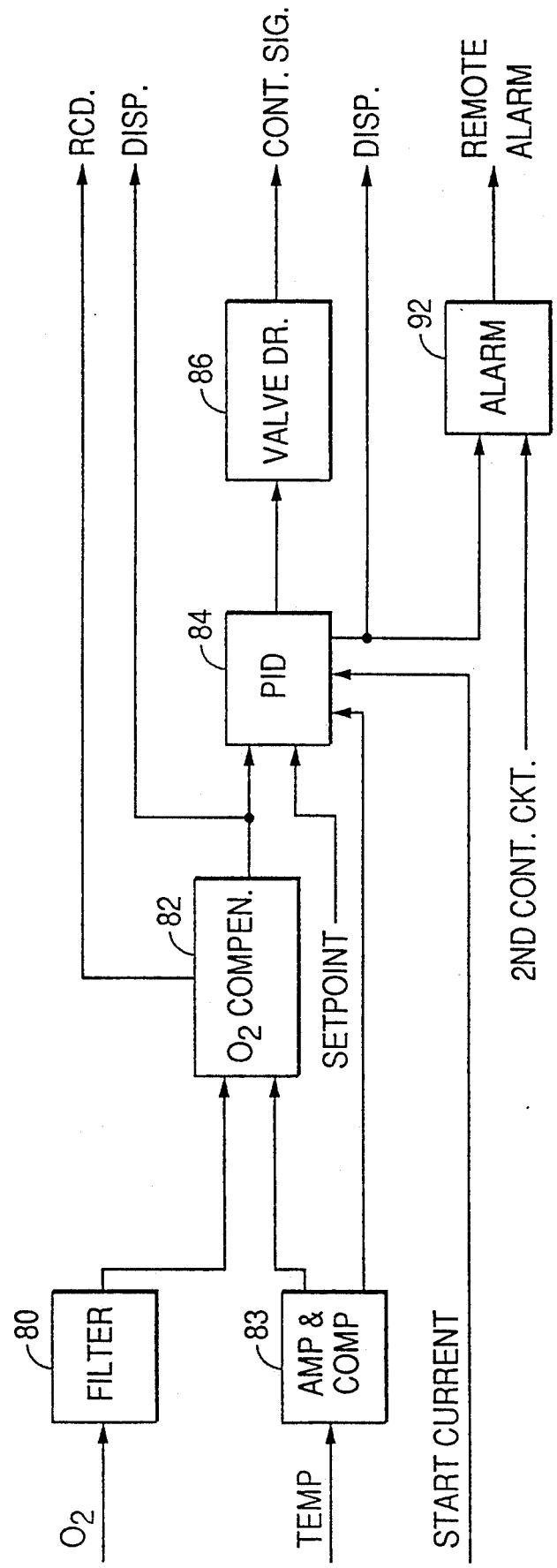
FIG. 4 is a block diagram showing the major components of the temperature compensated air/fuel ratio controller made in accordance with the principles of the present invention.

FIG. 4 illustrates, in block diagram form, one circuit providing linear and non-linear temperature compensation for the oxygen content signal. An oxygen content signal, in millivolts, is applied to active filter 80. The filtered oxygen sensor signal is applied to oxygen compensataion circuit 82. The temperature signal (approximately 0.0–0.03 volts) is applied to amplifier and comparator circuit 83. This circuit conditions the temperature signal. The conditioned temperature signal is applied to oxygen compensation circuit 82. The oxygen compensation circuit modifies the oxygen content signal, in one embodiment, by adding compensatory signals 22 and 20, as well as compensatory signal 18, to the filtered oxygen content signal applied at its input. The compensated oxygen content signal is then applied to PID 84. PID 84's output is applied to a valve driver 86. Valve driver 86 generates a pressurized gas control signal (Cont. Sig.) on control line 72 (FIG. 3) which operates as a control signal for fuel pressure regulator 54 (FIG. 3).

The operator also inputs a set point, which represents the desired air/fuel ratio operating point, to the PID controller 84. The PID controller 84 then works to adjust the air/fuel ratio such that the compensated oxygen voltage from circuit 82 matches this operator set point. Below 600° F., the comparator in circuit 83 (FIG. 4) disables the PID controller 84 and the operator input start current is connected to the valve driver. PID controllers are known in the art.

There are various signals in the front end of the controller which can be used to monitor the control loop and engine. One of these monitoring signals RCD is the compensated oxygen sensor voltage. This provides a representative signal indicative of the oxygen content of the exhaust gases from the internal combustion engine. This compensated oxygen content signal can be fed to a recording device. Additionally, the compensated oxygen content signal is displayed (DISP.) on a display device associated with the controller. From PID 84, one signal, representative of the output of the PID, is fed to the controller display (DISP.) and the same signal is fed to an alarm circuit 92. If a second controller is used to control a dual bank, internal combustion engine, the signal representative of the output of PID 84 from the second control circuit is fed into alarm circuit 92. The output of alarm circuit 92 is applied to an external alarm module. The following Display Table shows a typical status display (using liquid crystal display) for the air/fuel ratio controller.

DISPLAY TABLE

| Air/Fuel Ratio | PID Status (One for Each Bank) |
|---|---|
| 9 Segment Bar Graph. Switch selectable left and right bank on dual bank controller. | Control Limit Rich/Lean of Set Point Low Temp Low Sensor Out |

Figure 5:
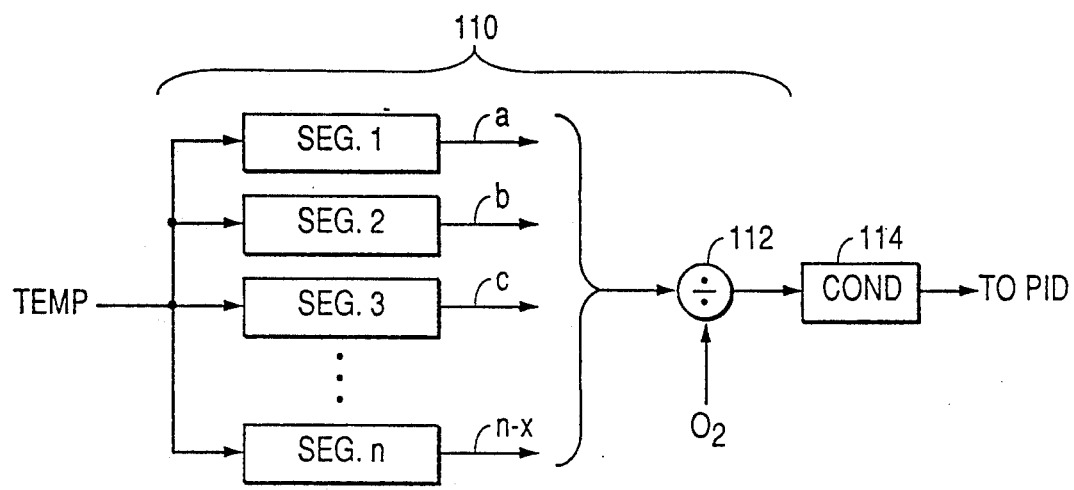
FIG. 5 diagrammatically illustrates one method of compensating the linear and non-linear signal portions of the oxygen content signal based upon the temperature range.

FIG. 5 diagrammatically illustrates a circuit for implementing the concepts of the present invention. If discrete components are used, the incoming temperature signal can be segmented into temperature regions within which the $O_2$ signal is relatively linear. As shown in FIG. 1, the non-linear portion of the oxygen content signal has been broken into three regions which are somewhat linear in nature. The first non-linear $O_2$ region is associated with compensatory signal segment 22, the second region is associated with compensatory signal region 20, and the third region is associated with compensatory signal segment 18. FIG. 5 diagrammatically illustrates that the oxygen compensation circuit 110 generates compensatory signal segments based upon temperature range segments 1, 2, 3 . . . n. These compensatory linear segments are based upon the predetermined curvilinear function of the oxygen signal the temperature curve shown in FIG. 1. Segment circuit 1 generates a first compensatory signal. Segment circuits 2 and 3 generate other compensatory signals based upon the temperature ranges identified at the front end of those control circuits. After compensatory signals a, b, c, $n_x$ are generated by the segment circuits, these compensatory signals are applied to summation point 112. Also, the filtered, but essentially unaltered, oxygen content signal is supplied to summation point 112. Thereafter, the summed and compensated oxygen content signal is applied to signal conditioner circuit 114 and ultimately to the PID controller.

Figure 6:
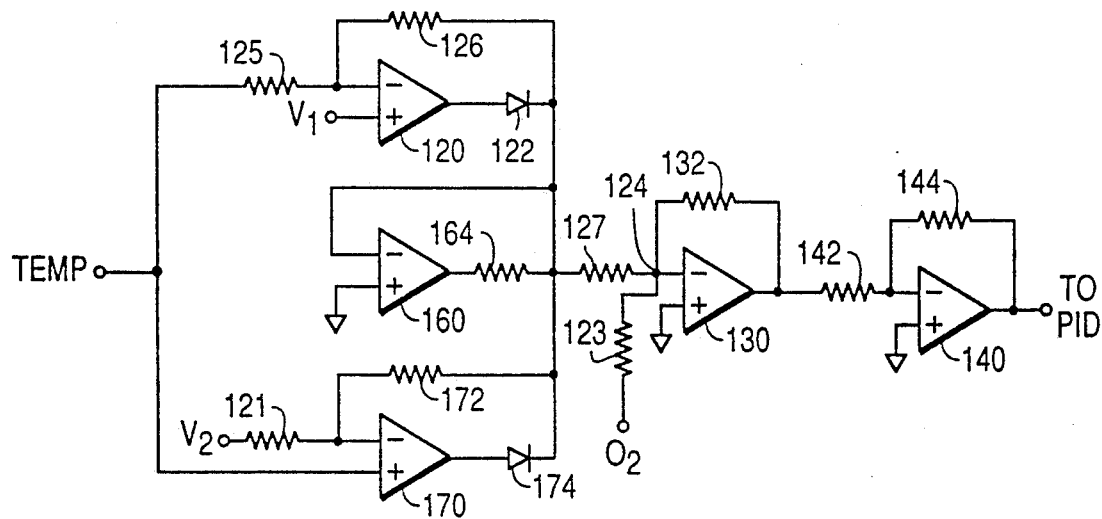
FIG. 6 is a block diagram showing one working embodiment of the temperature compensation circuit utilizing discrete electrical components in accordance with the principles of the present invention.

FIG. 6 shows the major components of a discrete circuit implementing a three-segment, non-linear oxygen compensation circuit. The temperature signal is applied to amplifier 120. Voltage $v_1$ is set to identify the temperature corresponding to the intersection of compensatory signal segments 22 and 20 shown in FIG. 1. The output of amplifier 120 is fed through diode 122 and the compensatory signal segment is then applied to summation point 124. Resistors 125 and 126 and any other complementary resistors associated with amplifier 120, are used to bias the signal and obtain the correct slope on compensatory signal 22, shown in FIG. 1. Resistors 123 and 127, operational amplifier 130 and resistor 132 operate as a summer for junction 124. The circuit consisting of operational amplifier 140 and resistors 142 and 144 provide signal conditioning for the compensated oxygen content signal. With respect to the second segment (represented by compensatory signal 20 in FIG. 1), operational amplifier 160 and resistor 164 assure zero compensation voltage is applied to summation point 124 when the temperature is in the range of segment 20. With respect to the third segment, operational amplifier 170 and resistor 172 are set to operate at the intersection of compensatory signal segments 20 and 18 (FIG. 1) and beyond and also to generate the slope of compensatory signal 18 shown in FIG. 1. Diodes 122 and 174 and resistor 164 assure the most positive voltage from amplification circuits 120, 160, or 170 is applied to summation point 124. Voltage $v_2$ is used to locate the temperature break point or intersection between compensatory signal segments 20 and 18.

A quad or four-way operational amplifier integrated circuit can be used wherein operational amplifiers 120, 130, 160 and 170 are found on a single integrated circuit. Operational amplifier 140 is shown as an inverter to provide a positive voltage output. The slopes of compensatory signal segments 22 and 18 are established by the ratio of resistances across operational amplifiers 120 and 170. Some of the resistors are not shown in the figure.

It is important to note that the present invention can be implemented as a microprocessor control loop. However, a microprocessor requires higher currents and power than the discrete circuitry disclosed hereinabove. In a microprocessor, a one to one correspondence table or a mathematical algorithm describing the curvilinear function of FIG. 1 would be used to generate a compensatory signal. For example, a look-up table would be used to generate a mirror image of the curvilinear function described in FIG. 1. The compensatory signal would be a mirror of curvilinear line A2.

The claims appended hereto are meant to cover modifications and changes within the spirit and scope of the present invention including both the discrete implementation of the circuitry and the microprocessor implementation.

What is claimed is:

1. A method for controlling an air/fuel ratio of an internal combustion engine comprising the steps of:
   electronically sensing the oxygen content and temperature of exhaust gas produced by said combustion engine and generating signals representative thereof;
   compensating both linear and non-linear variations of the oxygen content signal based upon said temperature signal; and,
   controlling said air/fuel ratio of said combustion engine based upon the compensated oxygen content signal.

2. A method as claimed in claim 1 wherein the step of electronically sensing includes the step of independently electronically sensing said oxygen content and said temperature of said exhaust gas.

3. A method as claimed in claim 1 wherein the steps of sensing, compensating and controlling include the step of establishing a feedback control loop for said engine.

4. A method as claimed in claim 3 wherein the steps of compensating and controlling include the step of maintaining the oxygen content signal within a predetermined signal range.

5. A method as claimed in claim 3 wherein the steps of compensating and controlling include the step of maintaining the oxygen content signal at a predetermined signal set point.

6. A method as claimed in claim 5 including the step of providing an operator input to establish the compensated oxygen content set point.

7. A method as claimed in claim 1 wherein said oxygen content signal varies as a curvilinear function of said temperature signal and said compensation step includes the step of compensating said oxygen content signal based upon a predetermined linear segmentation of said curvilinear function.

8. A method as claimed in claim 2 wherein the steps of sensing, compensating and controlling include the step of establishing a feedback control loop for said engine.

9. A method as claimed in claim 8 wherein the steps of compensating and controlling include the step of maintaining the compensated oxygen content signal at a predetermined signal set point.

10. A method as claimed in claim 9 including the step of providing an operator input to establish the oxygen content set point.

11. A method as claimed in claim 10 wherein said oxygen content signal varies as a curvilinear function of said temperature signal and said compensation step includes the step of compensating said oxygen content signal based upon a predetermined linear segmentation of said curvilinear function.

12. A temperature compensated air/fuel ratio controller for a carbureted internal combustion engine comprising:
An electronic oxygen content sensor and an electronic temperature sensor exposed to exhaust gas produced by said combustion engine, said sensors generating signals representative thereof;
means for compensating both linear and non-linear variations of the oxygen content signal based upon said temperature signal and generating compensated oxygen signals;
an air/fuel ratio controller receiving said compensated oxygen signals and generating control signals based thereon for said engine.

13. A controller as claimed in claim 12 wherein said controller is part of a feedback control system for said engine, said controller including an operator input which establishes a control set point for said compensated oxygen content signal and means for generating control signals for said engine such that said compensated oxygen content signal corresponds to said set point.

14. A controller as claimed in claim 12 wherein said controller is part of a feedback control system for said engine, said controller including an operator input which establishes a predetermined signal range for said compensated oxygen content signal and means for generating control signals for said engine such that said compensated oxygen content signal falls within said predetermined range.

15. A controller as claimed in claim 12 which is powered by less than approximately 100 milliwatts at approximately 3-4 volts AC RMS.

16. A controller as claimed in claim 12 wherein said oxygen sensor is a zirconium oxide sensor.

17. A controller as claimed in claim 15 wherein said oxygen content signal varies as a curvilinear function of said temperature signal and said means for compensating includes means for discretely segmenting the curvilinear response of said oxygen content signal as it varies with respect to said temperature signal and generating said compensated oxygen signals.

18. A controller as claimed in claim 13 which is powered by less than approximately 100 milliwatts at approximately 3-4 AC RMS.

19. A controller as claimed in claim 18 wherein said oxygen sensor is a zirconium oxide sensor.

20. A controller as claimed in claim 19 wherein said oxygen content signal varies as a curvilinear function of said temperature signal and said means for compensating includes means for discretely segmenting the curvilinear response of said oxygen content signal as it varies with respect to said temperature signal and generating said compensated oxygen signals.

* * * * *